(12) United States Patent
Kakimoto et al.

(10) Patent No.: US 8,676,294 B2
(45) Date of Patent: Mar. 18, 2014

(54) BRAIN DISEASE DIAGNOSIS SYSTEM

(75) Inventors: Akihiro Kakimoto, Hamamatsu (JP);
Yoshiyuki Shimizu, Hamamatsu (JP);
Tsuyoshi Kosugi, Hamamatsu (JP);
Hiroyuki Okada, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 292 days.

(21) Appl. No.: 13/002,371

(22) PCT Filed: Jun. 19, 2009

(86) PCT No.: PCT/JP2009/061224
§ 371 (c)(1),
(2), (4) Date: Jan. 3, 2011

(87) PCT Pub. No.: WO2010/004851
PCT Pub. Date: Jan. 14, 2010

(65) Prior Publication Data
US 2011/0105881 A1    May 5, 2011

(30) Foreign Application Priority Data
Jul. 7, 2008  (JP) .................. 2008-177254

(51) Int. Cl.
*A61B 5/05*    (2006.01)
(52) U.S. Cl.
USPC .......................................... 600/407
(58) Field of Classification Search
USPC .......................................... 600/407
See application file for complete search history.

(56) References Cited

U.S. PATENT DOCUMENTS

2005/0213832 A1*  9/2005  Schofield et al. ............. 382/240

FOREIGN PATENT DOCUMENTS

| JP | 2005-237441 | 9/2005 |
|---|---|---|
| JP | 2006-208250 | 8/2006 |
| JP | 2006-314778 | 11/2006 |
| JP | 2007-125370 | 5/2007 |
| JP | 2008-132320 | 6/2008 |
| WO | 2007/063656 | 6/2007 |

OTHER PUBLICATIONS

Korbinian Brodmann, "Brodmann's Localisation in the Cerebral Cortex: The Principles of Comparative Localisation in the ceregral Cortex Based on Cytoarchitectonics," Springer, p. 108, Chpt. IV.

* cited by examiner

*Primary Examiner* — Unsu Jung
*Assistant Examiner* — Saurel J Selkin
(74) *Attorney, Agent, or Firm* — Drinker Biddle & Reath LLP

(57) ABSTRACT

To perform a more accurate and detailed diagnosis of a brain disease, a diagnosis server of the brain disease diagnosis system for diagnosing a brain disease of an examined person includes: an acquiring unit for acquiring a brain image of the examined person so as to obtain an acquired image; a region setting unit for setting a plurality of regions in the acquired image; an individual index value calculating unit for calculating an individual index value based on a pixel value of the acquired image, in each of the plurality of regions; a whole index value calculating unit for calculating a whole index value by weighting the individual index value of each of the plurality of regions; a diagnosis unit for diagnosing the brain disease of the examined person based on the whole index value; and an output unit for outputting information indicating a diagnosis outcome.

8 Claims, 15 Drawing Sheets

*Fig.12*
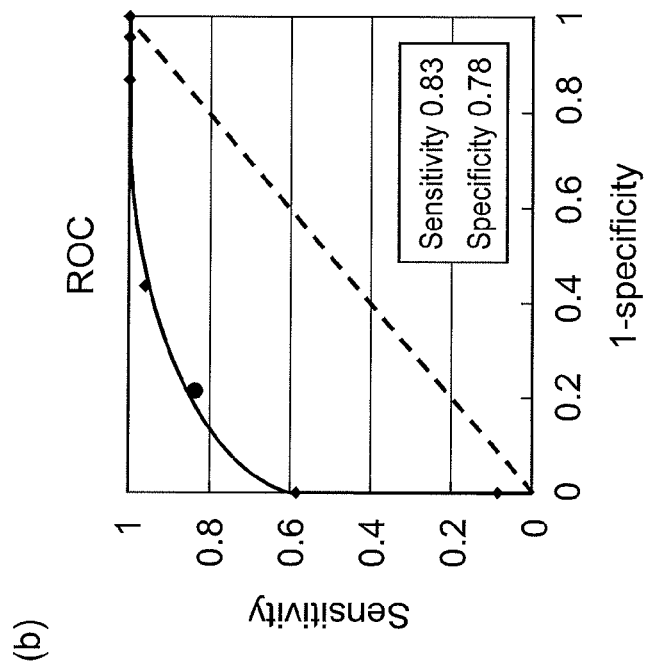
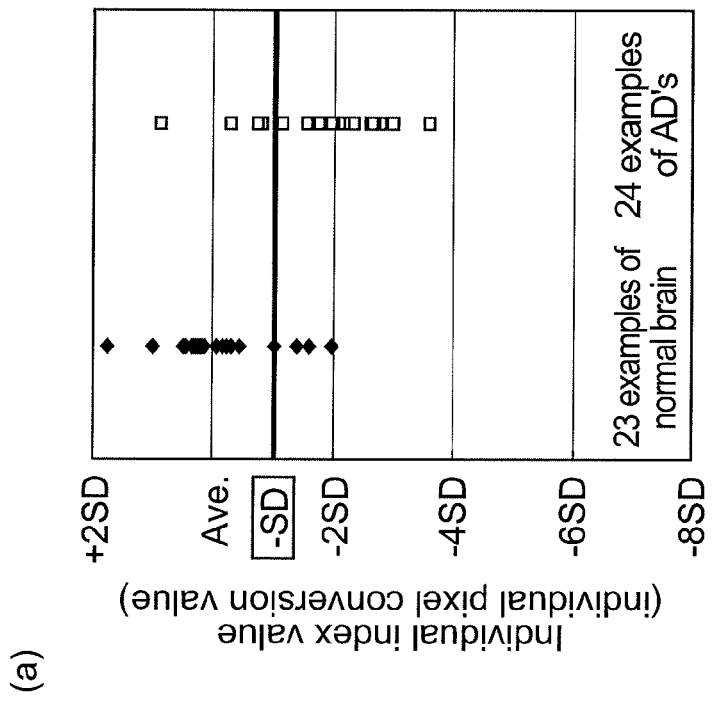

Fig. 14
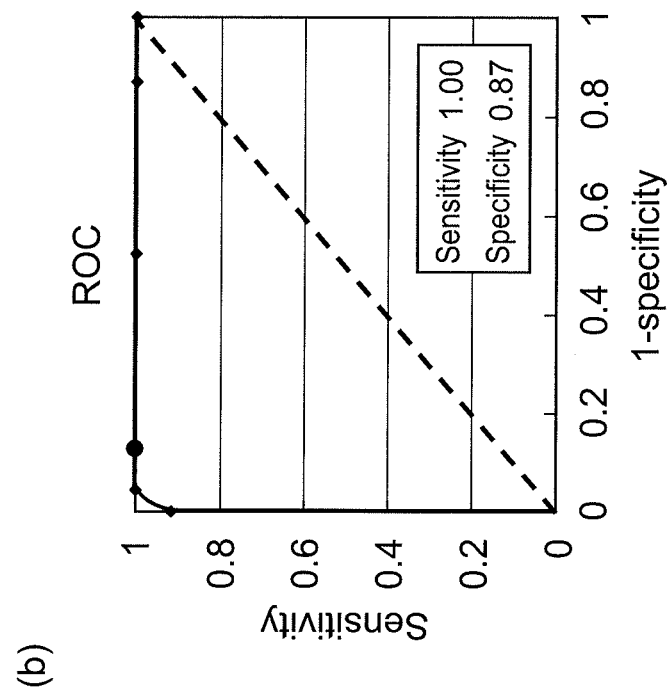
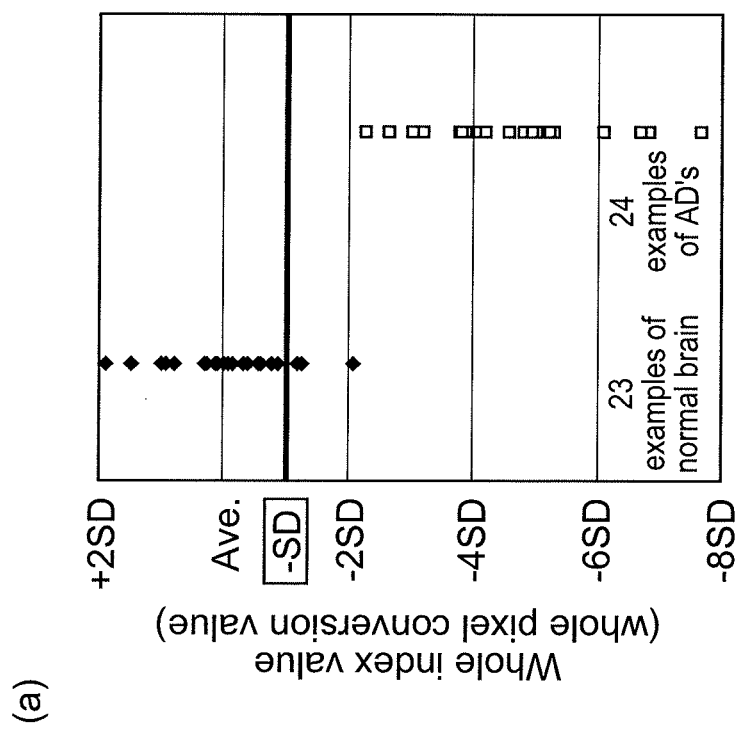

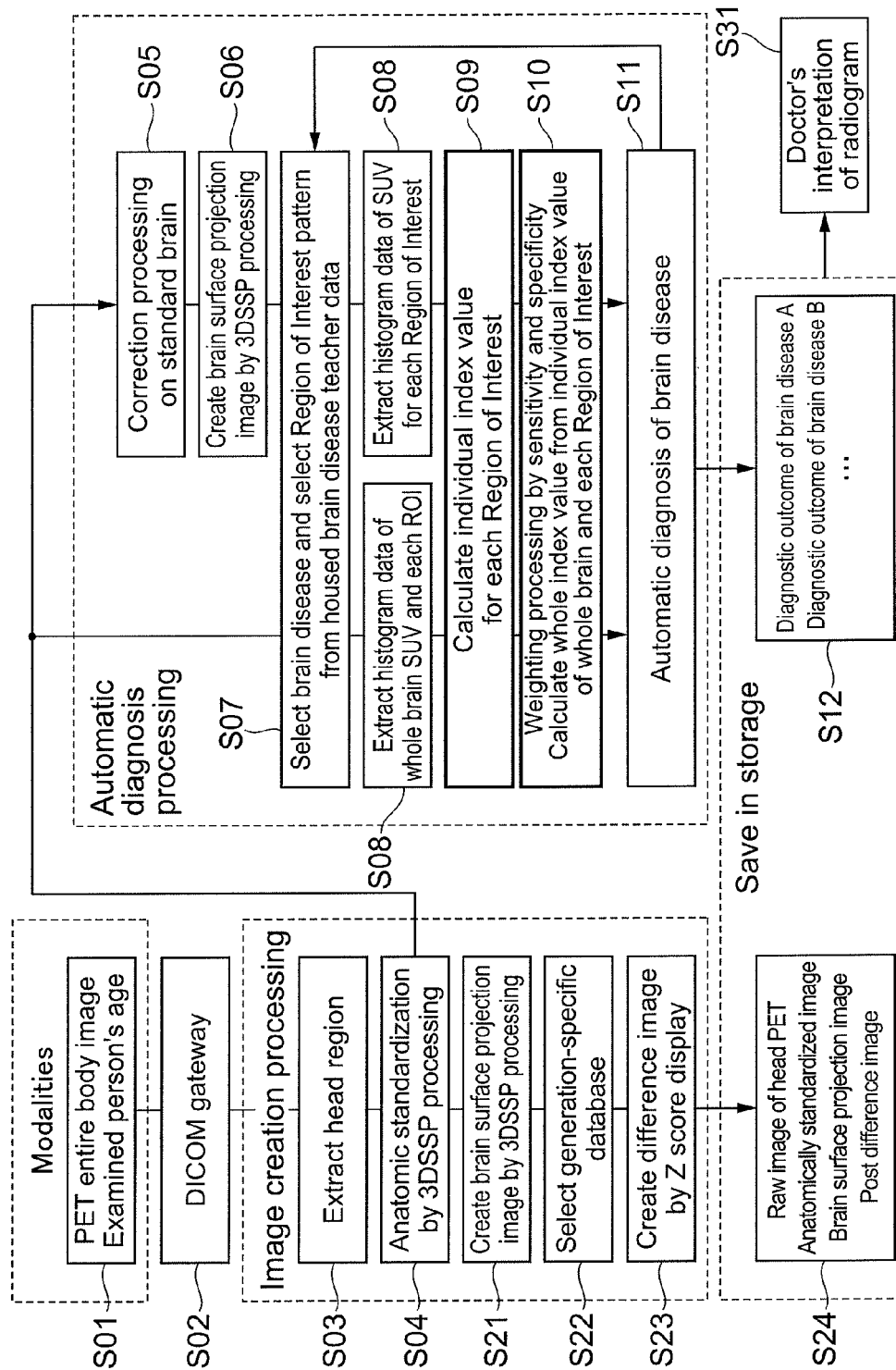

BRAIN DISEASE DIAGNOSIS SYSTEM

TECHNICAL FIELD

The present invention relates to a brain disease diagnosis system diagnosing a brain disease of an examined person.

BACKGROUND ART

Along with the development of medical technology, various information such as patient information and image information are being converted into electronic data. In particular, along with the development of medical devices, the image data amount has increased, and in response thereto, the burden imposed on doctors to interpret radiograms has increased. Under such circumstances, an automatic diagnosis system (Computer-aided diagnosis (CAD)) intended to assist a doctor in the interpretation of a radiogram is being researched and developed targeted for various modalities such as Computed Tomography (CT), Magnetic Resonance Imaging (MRI), ultrasonography (US), Single Photon Emission Computed Tomography (SPECT), and Positron Emission Tomography (PET), or sites (a lung field, a breast, etc.).

As a method for diagnosing a brain disease in the automatic diagnosis system, there is proposed a method described in Patent Literature 1. In this method, a cinerea tissue is extracted from a subject's brain image data obtained from MRI, PET, SPECT, etc., and the extracted brain image is smoothened. Thereafter, anatomic standardization, etc., are performed on the brain image to statistically compare the brain image of the subject and that of a healthy person after which a Region of Interest (ROI) is set for analysis. Then, the analysis result is provided as a diagnostic outcome. In this case, a region set as the ROI is automatically set based on a Z score calculated from an average value and a standard deviation of voxel values of a healthy person image cluster about each voxel of the brain image.

CITATION LIST

Patent Literature

Patent Literature 1: Japanese Published Unexamined Patent Application No. 2005-237441

SUMMARY OF INVENTION

Technical Problem

In the method described in the Patent Literature 1, a brain disease is diagnosed based on the analysis in which the automatically set single ROI is uniformly treated. However, it is probable that the analysis of only the single ROI does not permit exact diagnosis. Moreover, it is not possible to perform a detailed diagnosis to determine what brain disease occurs. This is due to the fact that when only the single ROI is analyzed, it is not possible to determine whether the data of the ROI results from an influence of a brain disease, nor is it possible to determine as to whether it results from an influence of what brain disease (whether it results from an influence of Alzheimer's, for example).

The present invention has been achieved to solve the above-described problems, and an object thereof is to provide a brain disease diagnosis system capable of performing a more accurate and detailed diagnosis of a brain disease.

Solution to Problem

In order to achieve the above-described object, a brain disease diagnosis system according to the present invention is a brain disease diagnosis system for diagnosing a brain disease of an examined person which includes: acquiring means for acquiring a brain image of the examined person so as to obtain an acquired image; region setting means for setting a plurality of regions in the acquired image acquired by the acquiring means; individual index value calculating means for calculating an individual index value based on a pixel value of the acquired image, in each of the plurality of regions set by the region setting means; whole index value calculating means for calculating a whole index value by weighting the individual index value of each of the plurality of regions calculated by the individual index value calculating means; diagnosis means for diagnosing the brain disease of the examined person based on the whole index value calculated by the whole index value calculating means; and output means for outputting information indicating a diagnosis outcome issued by the diagnosis means.

In the brain disease diagnosis system according to the present invention, based on the image of the brain of the examined person, the brain disease of the examined person is diagnosed. In this system, a plurality of regions are set to the brain image, and individual index values based on the pixel value are calculated for each of the plurality of regions. Then, each of the individual index values is weighted so that a whole index value is calculated after which the above-described diagnosis is performed from the whole index value. Therefore, based on the brain disease diagnosis system according to the present invention, it is possible to make a determination in which an influence of a brain disease is considered for each brain region and also possible to perform a more accurate and detailed diagnosis of the brain disease.

Desirably, the diagnosis means diagnoses the brain disease of the examined person by comparing a threshold value obtained based on an index value of sample data having the brain disease and an index value of sample data not having the brain disease and the whole index value calculated by the whole index value calculating means. According to this configuration, the criteria for determination at the time of the determination using the whole index value can be made more appropriate, and further, it is possible to perform a more accurate and detailed diagnosis of the brain disease.

Desirably, the whole index value calculating means performs the weighting based on the index value of the sample data having the brain disease and the index value of the sample data not having the brain disease. According to this configuration, the weighting can be performed more appropriately at the time of the calculation of the whole index value. For example, a large weighting can be applied to a range where the brain disease to be diagnosed is greatly influenced. As a result, it is possible to perform a more accurate and detailed diagnosis of the brain disease.

Desirably, the acquiring means corrects the image based on the pixel value of the acquired brain image so as to obtain the acquired image. According to the configuration, the brain disease can be appropriately diagnosed by removing an individual variability, etc., of the brain of the examined person.

Desirably, the acquiring means also acquires information indicating the age of the examined person, and the diagnosis means diagnoses the brain disease of the examined person according to the age of the examined person indicated by the information acquired by the acquiring means. Although, generally, a state of a brain changes according to age, according to this configuration, it is possible to appropriately diagnose a brain disease according to age.

Desirably, the acquiring means anatomically standardizes the acquired brain image so as to obtain the acquired image.

According to this configuration, it is possible to appropriately diagnose a brain disease by facilitating the processing of the brain image.

Desirably, the brain disease diagnosis system further includes imaging means for imaging the brain image of the examined person, wherein the acquiring means acquires the image imaged by the imaging means. According to this configuration, the brain image can be reliably acquired, and thus, the present invention can be reliably implemented.

Desirably, the imaging means images a slice image of a brain of the examined person as the brain image of the examined person, and the acquiring means produces from the slice image imaged by the imaging means a brain surface projection image obtained by projecting a brain surface so as to obtain the acquired image. According to this configuration, based on the brain surface image that facilitates the diagnosis for some type of a brain disease, the diagnosis can be performed.

Advantageous Effects of Invention

According to the present invention, it is possible to make a determination while considering an influence of a brain disease for each brain region, thus performing a more accurate and detailed diagnosis of the brain disease.

BRIEF DESCRIPTION OF DRAWINGS

FIG. 12 are a graph showing an average value of SUV of a whole brain of an Alzheimer's diseased brain and a normal brain, for each of a plurality of examined persons, and a graph showing a relationship between a threshold value, and a sensitivity and a specificity.

FIG. 14 is a graph showing a whole index value of an Alzheimer's diseased brain and a normal brain, for each of a plurality of examined persons, and a graph showing a relationship between a threshold value, and a sensitivity and a specificity.

FIG. 15 is a flowchart showing processing executed in the brain disease diagnosis system according to an embodiment of the present invention.

DESCRIPTION OF EMBODIMENTS

Hereinafter, together with diagrams, a suitable embodiment of a brain disease diagnosis system according to the present invention will be explained in detail. It is noted that in the description of drawings, like components are denoted by like numerals and overlapping descriptions will be omitted.

Figure 1:
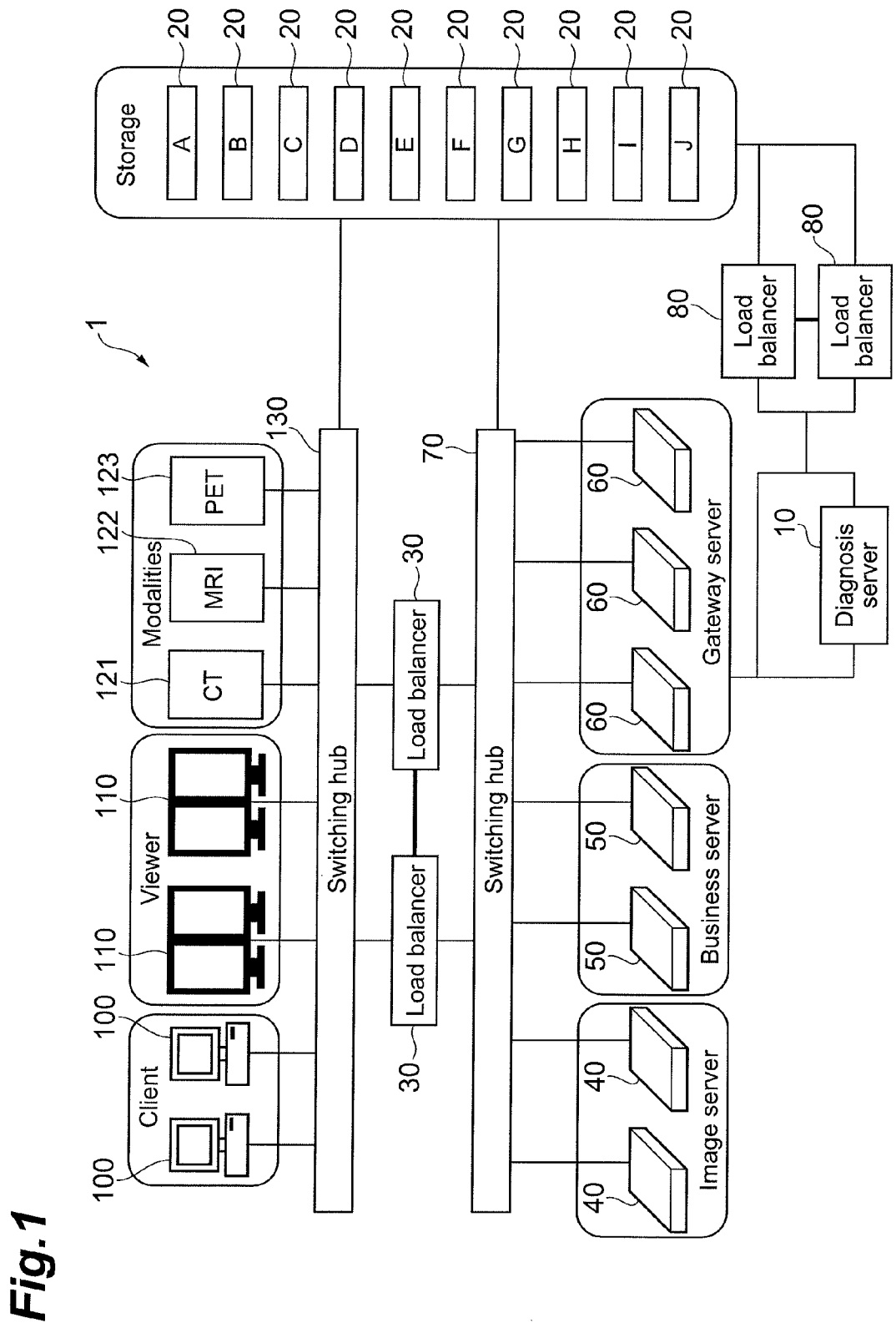
FIG. 1 is a diagram showing the configuration of a brain disease diagnosis system according to an embodiment of the present invention.

FIG. 1 shows the configuration of a brain disease diagnosis system 1 according to the embodiment. The brain disease diagnosis system 1 is a system diagnosing a brain disease of an examined person. That is, the brain disease diagnosis system 1 is a system for determining whether the examined person suffers from a brain disease. Examples of a brain disease subject to diagnosis may include a disease the type of which is specified such as Alzheimer's disease and a disease the type of which is not specified in which whether an abnormality occurs in a brain is not known. In this embodiment, Alzheimer's disease is used as an example.

As shown in FIG. 1, the brain disease diagnosis system 1 is configured to include a diagnosis server 10 that serves a primary function of the brain disease diagnosis system 1. Moreover, it is desired that the brain disease diagnosis system 1 includes a storage system in which medical image data imaged by modalities such as a CT machine, an MRI machine, and a PET machine is accommodated and managed, or the system 1 is connected to these machines. In this embodiment, as described below, the brain disease diagnosis system 1 includes the storage system; however, the system 1 does not necessarily include the storage system.

The brain disease diagnosis system 1 (as the configuration of the storage system) includes: a plurality of storages 20 for accommodating image data; a plurality of load balancers 30; a plurality of image servers 40; a plurality of business servers 50; and a plurality of gateway servers 60.

Each load balancer 30 is a device for performing various processing such as receiving a task request input to the storage system, and in response to the task request, transferring it to each of the servers 40, 50, and 60 of the storage system. Each load balancer 30 performs load distribution control so that each of the servers 40, 50, and 60 is not overloaded for each task request. The load balancer 30, the storages 20, and each of the servers 40, 50, and 60 are connected through a wired line via a switching hub 70 so that information can be transmitted and received to and from each other. It is noted that one of the two load balancers 30 is used as a back-up, for example, in a case where one of the two experiences a failure.

Each image server 40 is a device for recording and managing information about the image data. Specifically, the information about the image data indicates in which of the storages 20, out of the plurality of storages 20, the image data is accommodated (accommodation storage information). The image server 40 is input with a write request and a read request of the information from the load balancer 30, and performs processing in response to the requests. Moreover, the image servers 40 are connected to each other through a wired line, and transmit and receive the information to and from each other. Between the image servers 40, the information is synchronized. Further, the image server 40 performs processing on an image imaged by the modalities, as described in more detail below.

Each business server 50 is a device for recording and managing information of the examined person about the image data. The business server 50 is input with a task request for processing about the information of the examined person from the load balancer 30, and performs processing in response to the request. Further, similar to the image server 40, the business servers 50 are connected through a wired line, and can transmit and receive the information to and from each other.

Each gateway server (DICOM gateway) 60 is a device that is input with the image data accommodated in the storages 20 from the load balancer 30 and transfers it to the storage 20. Each of the gateway servers 60 outputs the image data to the load balancer 80 connected to the storage 20. It is noted that this load balancer 80 is different from the load balancer 30 connected to each of the servers 40, 50, and 60. Further, when information used for diagnosing the brain disease according to the embodiment is input, the gateway server 60 inputs the information to the diagnosis server 10.

The load balancer 80 determines which of the storages 20 in which the image data input from the gateway server 60 or the diagnosis server 10 or data indicating the diagnostic outcome should be accommodated, and accommodates the data into the determined storage 20. Generally, the above-described data is accommodated in the two storages 20 in order to prevent a data loss. It is noted that one of the two load balancers 80 is used as a back-up, for example, in a case where one of the two experiences a failure.

Moreover, the brain disease diagnosis system 1 may include, as a device used by a user, a client 100, a viewer 110, and modalities 121, 122, and 123 in a manner to be connected to the storage system. Each of the above-described devices 100, 110, and 121 to 123 is connected to the load balancer 30 through a wired line via the switching hub 130 so that information can be transmitted and received to and from the load balancer 30.

The client 100 is a terminal used when the user utilizes the brain disease diagnosis system 1. The viewer 110 is a terminal for interpretation of a radiogram, for the user such as a doctor to interpret the image data. In the client 100 or the viewer 110, means for acquiring the image data and displaying the acquired image data is included. Moreover, the client 100 and the viewer 110 are used also for the user to refer to the diagnostic outcome provided by the brain disease diagnosis system 1. The client 100 and the viewer 110 input (by user's manipulation, for example) a request for acquiring the image data into the load balancer 30 in order to acquire the image data. In the request for acquiring, information for specifying the image data to be acquired is included.

The modalities 121 to 123 are machines or imaging means for imaging a head (brain) of the examined person to acquire the image data, and specifically are a CT machine 121, an MRI machine 122, and a PET machine 123, for example. In order to manage the acquired image data in the storage system, the modalities 121 to 123 send a request for registering the image data to the load balancer 30.

Further, the image data imaged by the modality 121 is a slice image, cut along a predetermined cross section, showing the interior of the head (brain) of the examined person. It is noted that the slice image desirably includes a plurality of slice images on a cross section at intervals of several mm to several cm, for example. Pixels configuring the slice image have intensity (pixel value) according to tissues or a region in the head, at a position corresponding to the pixels. For example, a pixel value of the slice image acquired by the PET machine 123 is a value according to Standard Update Value (SUV) or semi-quantitative amount indicating a cerebral glucose metabolic amount (SUV can be obtained by performing a predetermined arithmetic calculation on the pixel value. Alternatively, the pixel value itself can be used as a value indicating SUV). That is, the slice image used in the embodiment includes a pixel value according to a function depending on a position of the brain. In the embodiment, the slice image imaged by the above-described PET machine 123 is used for diagnosing the brain disease. Further, when the slice image is acquired by the PET machine 123, information indicating an age of the examined person is input as a result of input by a manipulator of the PET machine 123, for example, and the input information is made to correspond to the above-described slice image.

Specific examples of the above-described diagnosis server 10, storages 20, load balancers 30 and 80, image server 40, business server 50, gateway server 60, client 100, and viewer 110 include a computer provided with Central Processing Unit (CPU), a memory, a disc device, etc. When these are operated, functions of the respective devices are demonstrated.

Herein, a brain image processed in the brain disease diagnosis system 1 and information shown about the brain image will be explained in detail. A content to be explained here includes knowledge obtained through studies by the inventors of the subject application.

An image initially acquired in the brain disease diagnosis system 1 is based on the examined person's slice image acquired by the PET machine 123. In the brain disease diagnosis system 1, processing for imaging by the PET machine 123, and processing in which the image taken by the PET machine 123 is adopted as an acquired image (described later) by the diagnosis server 10 are performed. These processings are described below. It is noted that when the slice image is input to the diagnosis server 10, the information indicating the age of the examined person is also input in a corresponding manner, as described above, which makes the information indicating the age of the examined person available.

Figure 2:
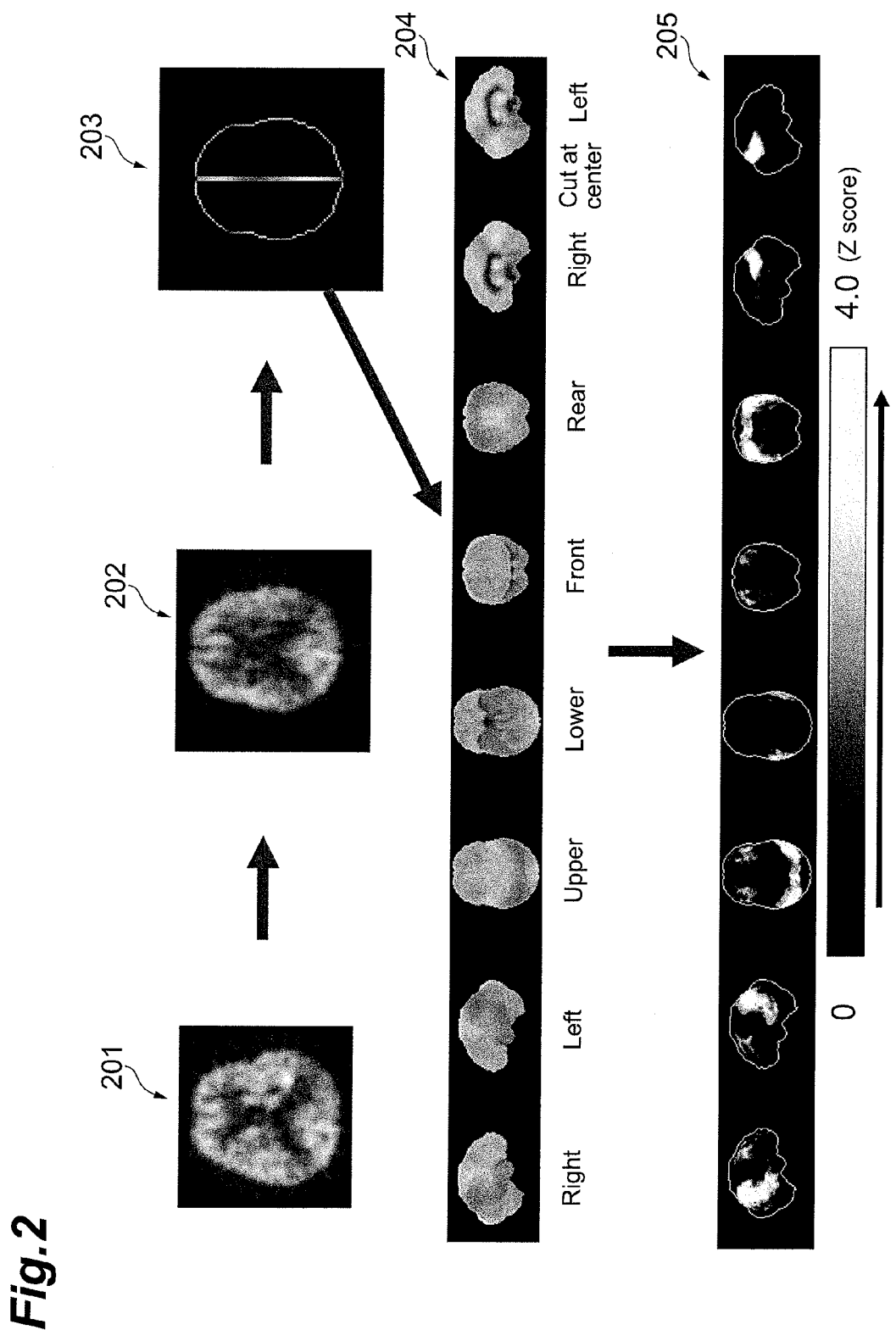
FIG. 2 is a view showing a brain image utilized in the brain disease diagnosis system.

The PET machine 123 images (the brain of) the examined person to acquire a slice image (PET raw image) 201 shown in FIG. 2. The PET machine 123 outputs the acquired slice image 201 to the diagnosis server 10 via the switching hub 130, the load balancer 30, the switching hub 70, and the gateway server 60. The diagnosis server 10 anatomically standardizes the input slice image 201 to obtain a standard brain image (tomographic image) 202 shown in FIG. 2. It is noted that in a case where the slice image acquired by the PET machine 123 is an image showing an entire human body, the diagnosis server 10 cuts out only a head image necessary for the diagnosis.

In this case, the anatomic standardization may be performed by a conventional method, and specifically, it is performed by using a tool of three dimensional stereotactic surface projection (3DSSP), for example. Subsequently, the diagnosis server 10 performs mask processing on the standard brain image 202 and cuts surrounding noise to extract image data inside the brain. It is noted that the above-described mask processing can be performed by using a conventional method. However, it is not always necessary to implement the above-described mask processing.

Subsequently, the diagnosis server 10 performs correction processing on the standard brain image 202 on which the anatomic standardization or the mask processing has been performed. In this correction processing, standardization is performed to alleviate a variation of the pixel values among the images. Specifically, the standard brain image 202 is corrected (for example, the pixel value is multiplied by a coefficient that could make an average of the pixel values a predetermined value) so that an average of the pixel values of the whole brain is a previously set predetermined value or a constant value. It is noted that the average of the pixel values of the whole brain may not always be constant; for example, the standard brain image 202 may be corrected so that an average of pixel values of a portion equivalent to a cerebellum, a pons or a thalami of the standard brain image 202, for example, is the previously set predetermined value.

Subsequently, the diagnosis server 10 generates a brain surface image 203 indicating a brain surface, as shown in FIG. 2, from the corrected standard brain image 202. The diagnosis server 10 generates a brain surface projection image 204 obtained by projecting the generated brain surface image from each direction. The brain surface projection image 204 is generated for each projected direction, and the directions are eight directions, i.e., right; left; upper; lower; front; rear; and right and left cut at the center, as shown in FIG. 2. Specifically, the brain surface image 203 and the brain surface projection image 204 are generated by processing utilizing a tool by the above-described 3DSSP.

Subsequently, processing further performed on the standard brain image 202 in the diagnosis server 10 will be explained. In the diagnosis server 10, the brain surface projection image 204 is generated from the standard brain image 202 according to a method similar to that described above. Next, an image 205 obtained by comparing the brain of the examined person to a normal brain is generated. A normal brain is a brain of an examined person who does not suffer from a brain disease. The brain surface projection image of a normal brain, similar to that described above, is previously acquired by the present system 1, etc., and accommodated in the storages 20 available. The diagnosis server 10 acquires the brain surface projection image of a normal brain from the storages 20. The brain surface projection images of a normal brain accommodated in the storages 20 are accommodated chronologically, and based on the information indicating the age of the examined person, the brain surface projection image of a normal brain at the same generation of the examined person is acquired. The diagnosis server 10 calculates an average value and a standard deviation of pixel values of the acquired brain surface projection image of a normal brain. Subsequently, based on the calculated value, the diagnosis server 10 calculates a Z score by using the equation below for each pixel of the brain surface projection image of the brain of the examined person. It is noted that an equation for calculating the Z score is previously stored in the diagnosis server 10.

Z score=(pixel value of brain of examined person-normal brain average value)/normal brain standard deviation The Z score indicates a degree by which the pixel value differs from the pixel value of a normal brain. When the PET image is used, the higher the value of the Z score, the lower the glucose metabolic amount. The diagnosis server 10 generates an image 205 obtained by comparing the brain of the examined person shown in FIG. 2 to a normal brain, in which the calculated Z score is used as the pixel value.

The diagnosis server 10 accommodates the brain image (image data) generated in this way, into the storages 20. It is noted that upon accommodation into the storages 20, the information indicating the age of the examined person and indicating whether the examined person has had a brain disease, etc., is accommodated in the storages 20 in a manner to correspond to the brain image so that the generated brain image can be used as comparison data when a brain of another examined person is diagnosed.

The examined person's slice image acquired by the PET machine 123 is also managed by the image server 40 of the storage system and accommodated in the storages 20.

Figure 3:
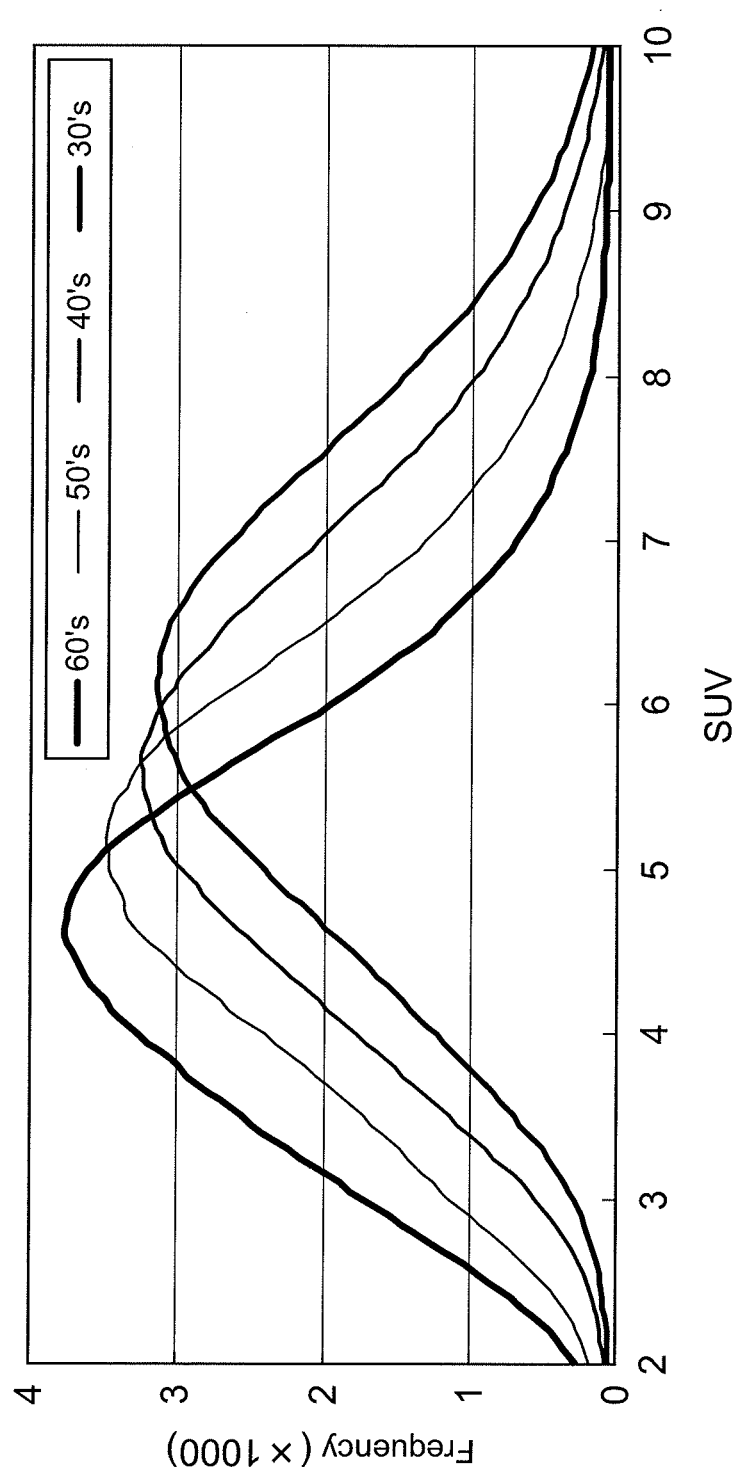
FIG. 3 is a graph showing a transition of whole cerebral metabolic amounts by aging, based on a standard brain image.

Herein, each brain image and the information shown about the brain image will be explained in detail. FIG. 3 shows a graph indicating a transition of the whole cerebral metabolic amounts by aging, based on the standard brain image 202. In this graph, a horizontal axis indicates SUV and a vertical axis indicates the frequency (pixel number) of the corresponding SUV in the standard brain image 202. The higher the frequency with large SUV, the larger the cerebral glucose metabolic amount. This graph is obtained by counting the frequency when the whole brain is the target, and provides an average of data of a plurality of examined persons (data items of 291 persons (237 men and 54 women) in their 30's, 397 persons (303 men and 94 women) in their 40's, 249 persons (121 men and 128 women) in their 50's, and 30 persons (30 men) in their 60's, respectively). As shown in FIG. 3, SUV is distributed so that SUV becomes smaller as the generations become older, and this indicates that the cerebral glucose metabolic amount becomes smaller as the generations become older. As described above, SUV in the brain image changes according to the age of the examined person.

Figure 4:
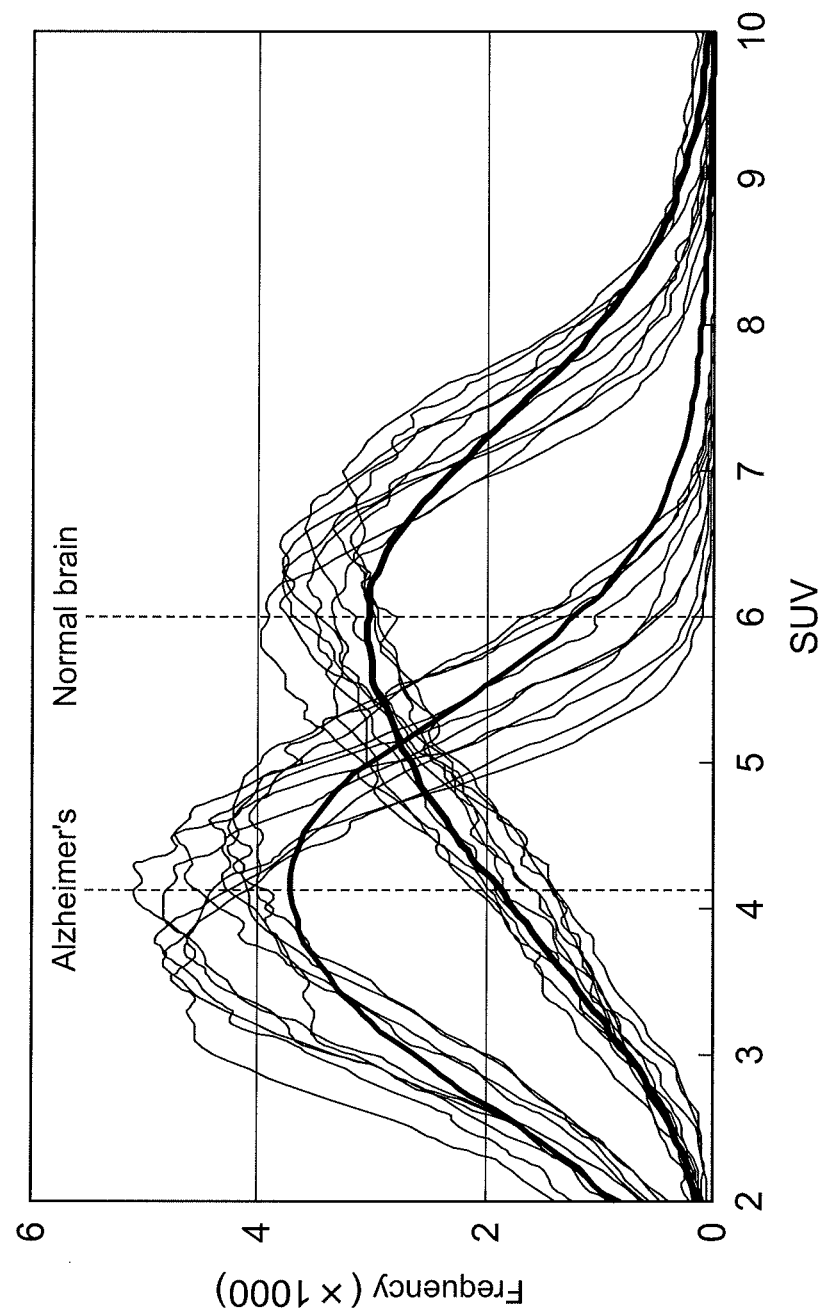
FIG. 4 is a histogram of SUV of an Alzheimer's diseased brain and a normal brain.
Figure 5:
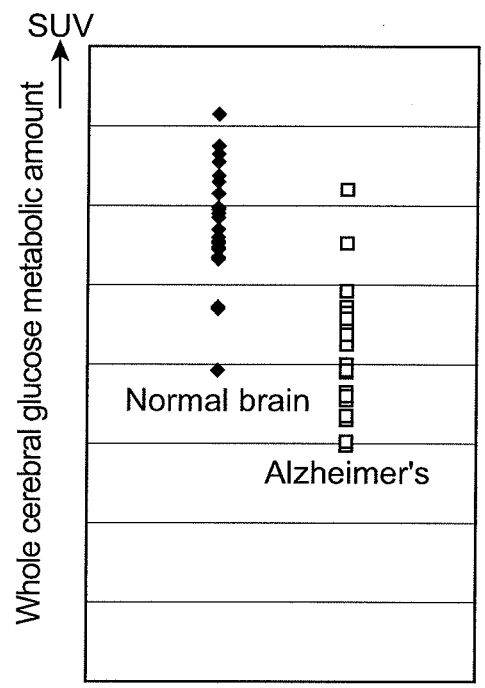
FIG. 5 is a graph showing an average value of SUV of an Alzheimer's diseased brain and a normal brain, for each of a plurality of examined persons.

FIG. 4 shows a graph indicating a difference in whole cerebral metabolic amounts between a normal brain and an Alzheimer's diseased brain, based on the standard brain image 202. In this graph, a horizontal axis indicates SUV and a vertical axis indicates the frequency (pixel number) of the corresponding SUV in the standard brain image 202. In this graph, the frequency is counted while using the whole brain as the target. Further, data indicated by a thin line in this graph is data of individual examined persons while data indicated by a thick line is data obtained by averaging the data of the examined persons, for each of an Alzheimer's diseased brain and a normal brain (data of 23 examined persons with a normal brain (12 men and 11 women, the average age 52.3 years old) and 24 examined persons with Alzheimer's disease (10 men and 14 women, the average age 58.3 years old), respectively). FIG. 5 is a graph showing an average value (vertical axis) of SUV, for each of the examined persons with an Alzheimer's diseased brain and with a normal brain. In the graph shown in FIG. 5, there is a significant difference (in average value of SUV) between a brain image of Alzheimer's disease and that of a normal brain where the level of significance is less than 0.001. As described above, depending on whether the examined person suffers from Alzheimer's disease, SUV in the brain image differs.

Figure 6:
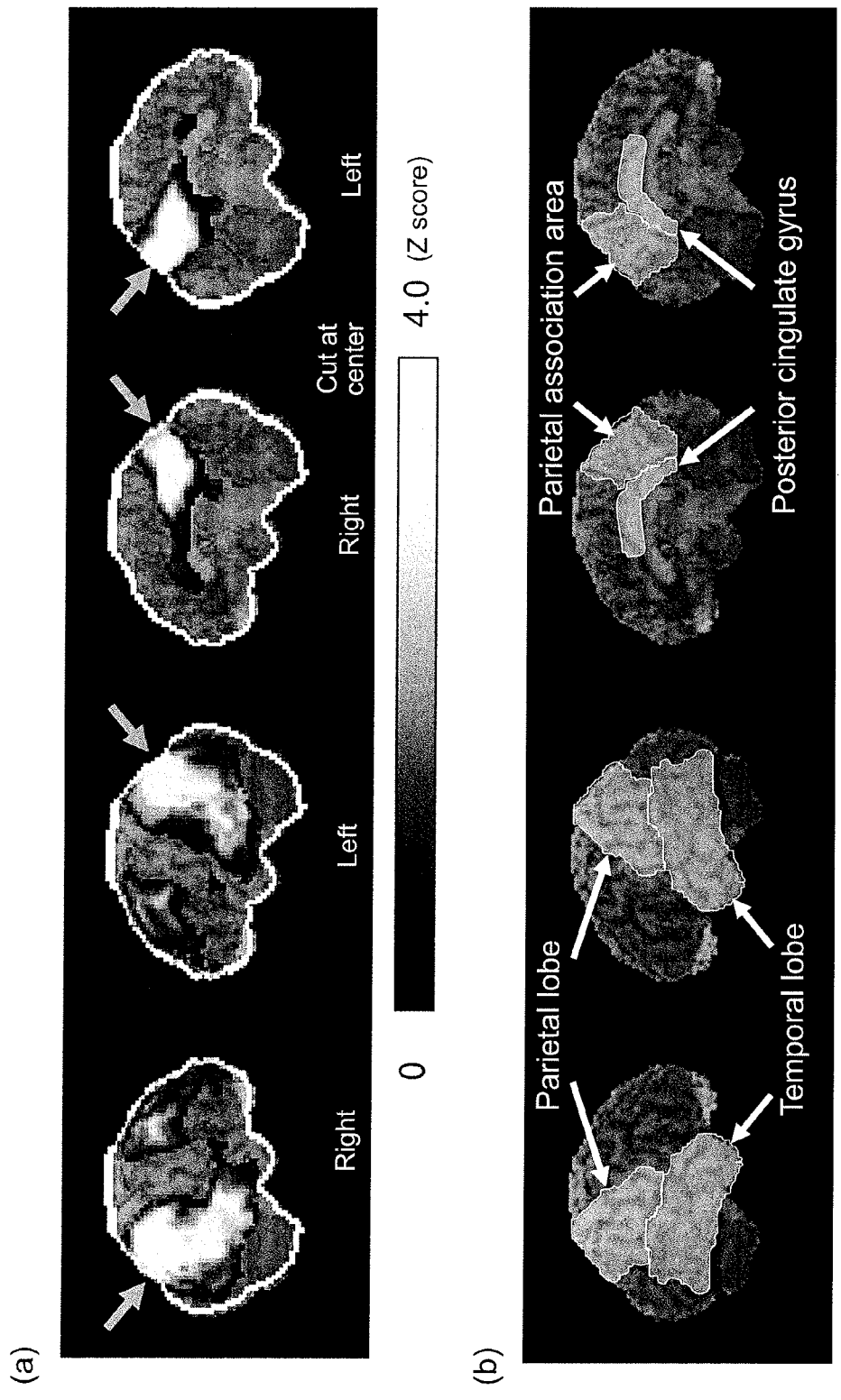
FIG. 6 are views showing an image according to a Z score obtained from a brain surface projection image of a patient with Alzheimer's disease when a brain surface projection image of a normal brain is to be compared, and also showing a brain site with a high Z score.

FIG. 6(a) shows an image that is according to the Z score calculated as described above where an average of the pixel values of the brain surface projection images of a plurality of patients with Alzheimer's disease (24 patients) is a target to be compared with an average value of the pixel values of the brain surface projection images of a plurality of patients with a normal brain (23 patients) (It is noted that the image is similar to the image 205 in FIG. 2). As shown in the image, portions with a high Z score, i.e., portions with a large difference in pixel value between an Alzheimer's diseased brain and a normal brain, are biased. The portions with a high Z score include portions of a cerebral parietal lobe, temporal lobe, parietal association area, and posterior cingulate gyrus (FIG. 6(b) shows corresponding locations of the brain image). As shown in the above figure, between an Alzheimer's diseased brain and a normal brain, the difference in the cerebral glucose metabolic amount corresponds to a cerebral site.

Thus, the brain image processed in the brain disease diagnosis system 1 and the information shown about the brain image have been explained.

Figure 7:
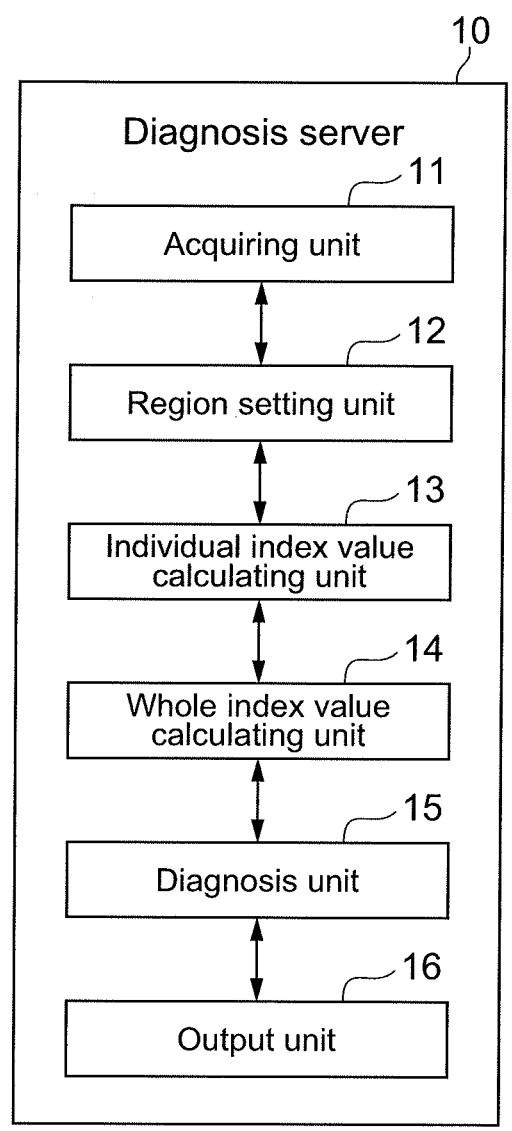
FIG. 7 is a diagram showing a functional configuration of a diagnosis server of a brain disease diagnosis system.

Subsequently, the functions, particularly functions of the diagnosis server 10, according to the present invention will be explained in detail. As shown in FIG. 7, the diagnosis server 10 is configured to include: an acquiring unit 11; a region setting unit 12; an individual index value calculating unit 13; a whole index value calculating unit 14; a diagnosis unit 15; and an output unit 16.

The acquiring unit 11 is acquiring means for acquiring the brain image of the examined person so as to obtain an acquired image. The image acquired by the acquiring unit 11 is an image which is acquired by the PET machine 123 and which is based on the examined person's slice image. As described above, the acquiring unit 11 is input with the slice image 201 via the gateway server 60 from the PET machine 123, and generates from the slice image 201 the standard brain image 202, the brain surface image 203, and the brain surface projection image 204 in this order by the above-described processing. The acquiring unit 11 uses the above-described standard brain image 202 and the brain surface projection image 204 as the acquired image used for diagnosing a brain disease. The acquiring unit 11 outputs the generated acquired image to the region setting unit 12. It is noted that the acquiring unit 11 does not always need to use the image on which the imaging processing has been performed as the acquired image, as described above. If the input brain image does not require imaging processing such as standardization and correction, then the respective imaging processing does not need to be performed (for example, the input brain image may be used as the acquired image).

The region setting unit 12 is region setting means for setting a plurality of regions (Regions of Interest: ROI) in the acquired image (standard brain image) input from the acquiring unit 11. When the region is set in the acquired image, the region is divided into cerebral anatomical sites, for example. FIGS. 8(a) and 8(b) show the cerebral anatomical sites. As shown in FIG. 8(a) depicting a right-side surface, the cerebral site includes a frontal lobe 301, a parietal lobe 302, a temporal lobe 303, an occipital lobe 304, and a cerebellum 305. Further, as shown in FIG. 8(b) depicting the right side obtained by cutting around the center of the brain, the cerebral site also includes a frontal association area 306, a posterior cingulate gyms 307, and a parietal association area 308. The whole brain may be set as a single region (in that case, an overlapping portion between the regions may occur). In the region setting, for example, setting such that coordinates in the image belong to which of the anatomical sites is previously performed (the information indicating the above is previously held), and then, based on the setting, the region is set. This setting is performed by an administrator, a doctor, etc., of the brain disease diagnosis system 1.

As a standard for specifying the anatomical site, an atlas of Talairach also used for standard brain conversion of 3DSSP and a brain map of Brodmann ([Korbinian Brodmann] Brodmann's Localisation in the Cerebral Cortex: The Principles of Comparative Localisation in the cerebral Cortex Based on Cytoarchitectonics) showing anatomical and cytoarchitectural categories of the cerebral cortex (classified from 1 to 52) may be used. Further, based on the brain map of Brodmann, several regions may be combined so that the regions are segmented in a large region such as a frontal lobe, a temporal lobe, a parietal lobe, an occipital lobe, and a cerebellum.

There is no need that the setting of a region is performed on the whole brain image, and the setting may be performed on a portion where the pixel value specifically changes due to a disease subject to diagnosis. For example, in the case of Alzheimer's disease, the parietal lobe, the temporal lobe, the parietal association area, and the posterior cingulate gyrus tend to change more easily, and thus, the respective regions may be set on these portions. That is, it is preferable that the region be set on a site where a change specific to the brain disease that is subject to examination is recognized. Conversely, the region may also be set on a site where the change specific to the brain disease that is subject to examination is not recognized. Moreover, the region may also be set on a site where the doctor often observes, and conversely, the region may be set on a site where the doctor seldom observes.

When the region is set, it may also be possible that the brain image of a normal brain acquired as a sample and the image of a brain that suffers from a disease subject to diagnosis are previously Z-scored for each pixel, as described above, and the region is automatically set for each value of the Z score, i.e., 0 to 0.5, 0.5 to 1.0, etc.

The region setting unit 12 outputs the acquired image and the information indicating the plurality of set regions, to the individual index value calculating unit 13.

The individual index value calculating unit 13 is individual index value calculating means for calculating, based on the pixel value of the acquired image, an individual index value of each of the plurality of regions set by the region setting unit 12. Specifically, the individual index value calculating unit 13 calculates the individual index value as follows: First, for each region set in the acquired image, frequencies of the pixel for each pixel value, as a value indicating SUV, are plotted in a histogram, as shown in FIG. 4. The individual index value calculating unit 13 calculates an average value of SUV, a standard deviation, a maximum value, a minimum value, an integral value, and a distribution pattern, from the histogram, and uses them as the individual index value.

In the embodiment, an example in which the average value of SUV and the standard deviation are used as the individual index value will be explained. Also, the individual index value may also be evaluated as follows: from sample data of an average value of a normal brain, an average value $N_{ave}$ and standard deviation $NL_{SD}$ of the pixel value are previously calculated, and by using these values and the following equation, an individual pixel conversion value x' of an average value x of the pixel value of the acquired image of the examined person is evaluated and used as the individual index value.

$$x' = \frac{1}{NL_{SD}} \times x - \frac{NL_{ave}}{NL_{SD}} \qquad \text{[Equation 1]}$$

The individual index value calculating unit 13 outputs information indicating the calculated individual index value to the whole index value calculating unit 14.

The whole index value calculating unit 14 is whole index value calculating means for weighting the individual index value of each region calculated by the individual index value calculating unit 13 so as to calculate a whole index value. Specifically, as shown in the following equation, the whole index value is calculated as follows: a weight coefficient kn set to each individual index value Rn (n is a numeral indicating a region) and the corresponding individual index value are multiplied and the resultant values are totaled.

Whole index value=$R1 \times k1 + R2 \times k2 + R3 \times k3 + \ldots + Rn \times kn$ Moreover, the above-described weight coefficient kn is desirably set based on an index value of sample data (of a brain image) having the brain disease and an, index value of sample data (of a brain image) not having the brain disease. The individual index value and the whole index value, and an attitude toward the diagnosis in the present invention will be explained in detail later. The weight coefficient is desirably set in a manner to significantly influence the whole index value in a region where there is a large difference (there is a tendency to differ) in individual index value between the brain of a cerebral disease and a normal brain. The whole index value calculating unit 14 outputs information indicating the calculated whole index value to the diagnosis unit 15.

The diagnosis unit 15 is diagnosis means for diagnosing a brain disease of the examined person based on the whole index value calculated by the whole index value calculating unit 14. Specifically, the diagnosis unit 15 compares a threshold value and the whole index value so as to diagnose whether the examined person suffers from a brain disease that is subject to examination. The above-described threshold value is previously stored by the diagnosis unit 15. In this case, the above-described threshold value is desirably a value obtained based on the index value of the sample data having a brain disease and the index value of the sample data not having the brain disease. Moreover, the diagnosis unit 15 may make a diagnosis to determine from the whole index value the degree by which the examined person suffers from the brain disease that is subject to examination. The diagnosis unit 15 outputs information indicating the diagnosis outcome to the output unit 16.

The output unit 16 is output means for outputting information indicating the diagnosis outcome by the diagnosis unit 15. Specifically, the output unit 16 provides that the doctor, etc., can refer to the diagnostic outcome by displaying the diagnostic outcome on a display device (not shown) arranged in the diagnosis server 10. Moreover, during the reference, the output unit 16 may display an image used for the diagnosis or data (age, etc.) of the examined person as well. Further, the information output by the output unit 16 may be accommodated in the storages 20 after which it is output. In this case, the data generated and calculated by each function is preferably accommodated in the storage at each calculation and generation.

Subsequently, processing from calculation of the whole index value by the whole index value calculating unit 14 to diagnosis of a brain disease by the diagnosis unit 15 will be explained in detail.

Figure 8:
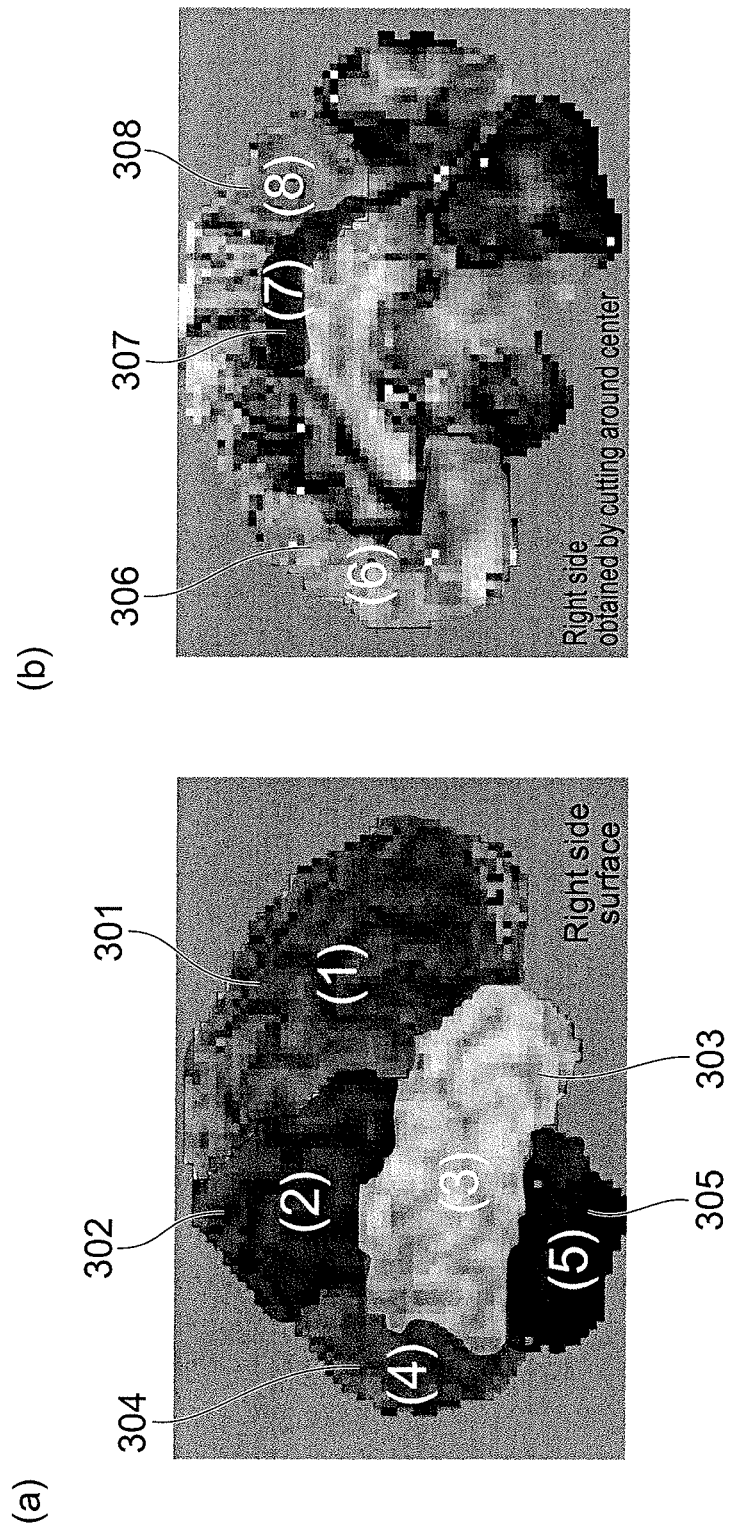
FIG. 8 are views showing an anatomical site of a brain.
Figure 9:
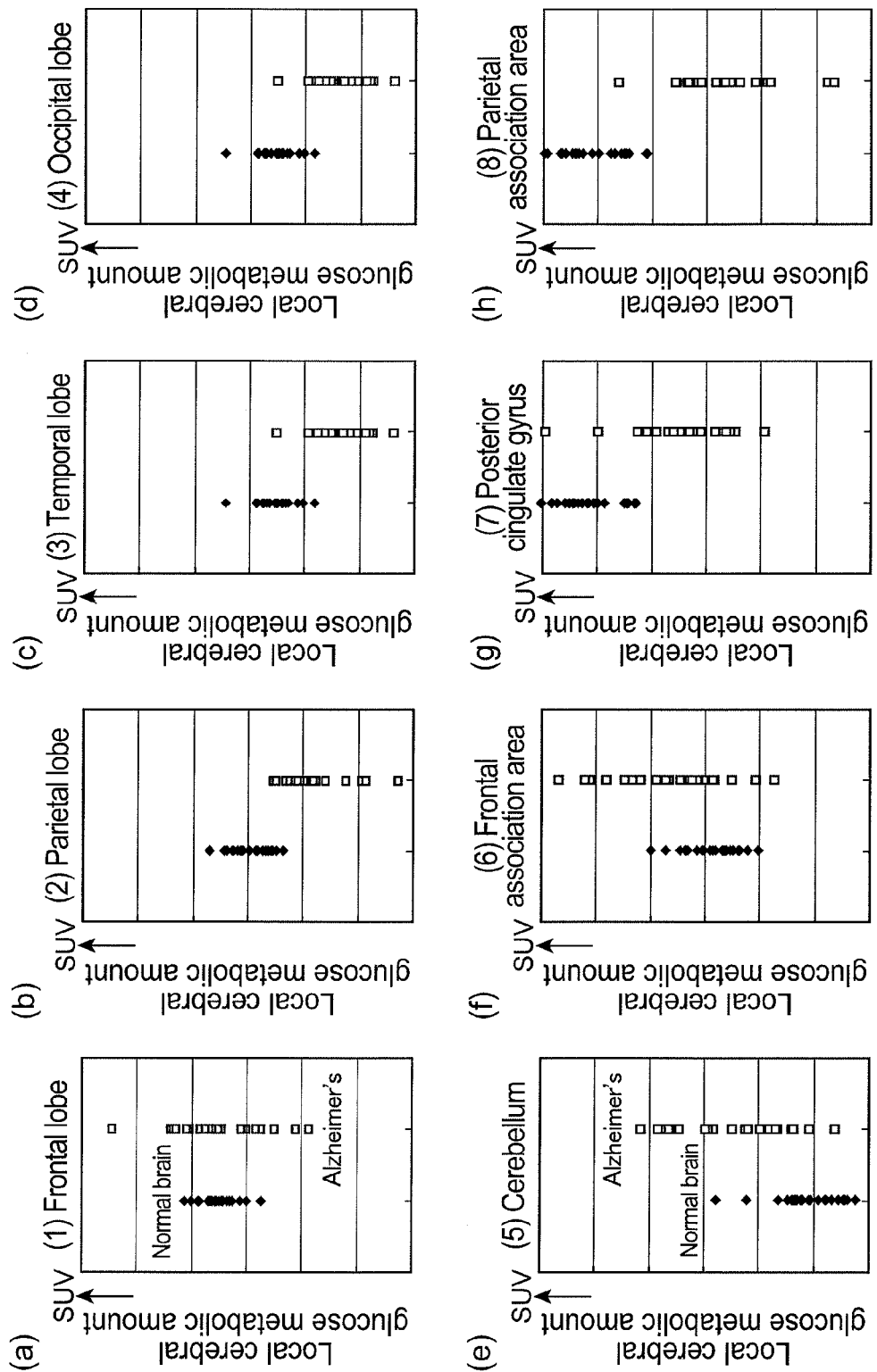
FIG. 9 is a graph showing an average value of SUV, calculated for each brain region, of an Alzheimer's diseased brain and a normal brain, for each of a plurality of examined persons.

FIG. 9 is a graph showing an average value (vertical axis) of SUV of an Alzheimer's diseased brain and a normal brain, for each of a plurality of examined persons, calculated for each brain region shown in FIG. 8 (the same graph as that in FIG. 5). In the graph shown in FIG. 9, there is a significant difference (in average value of SUV) between an image of an Alzheimer's diseased brain and that of a normal brain with the following levels of significance, respectively. The levels of the significance are as follows: less than 0.001 in the parietal lobe (2), less than 0.001 in the temporal lobe (3), less than 0.005 in the occipital lobe (4), less than 0.001 in the cerebellum (5), less than 0.005 in the frontal association area (6), less than 0.001 in the posterior cingulate gyms (7), and less than 0.001 in the parietal association area (8), respectively. It is noted that there is no level of significant in the frontal lobe (1).

Figure 10:
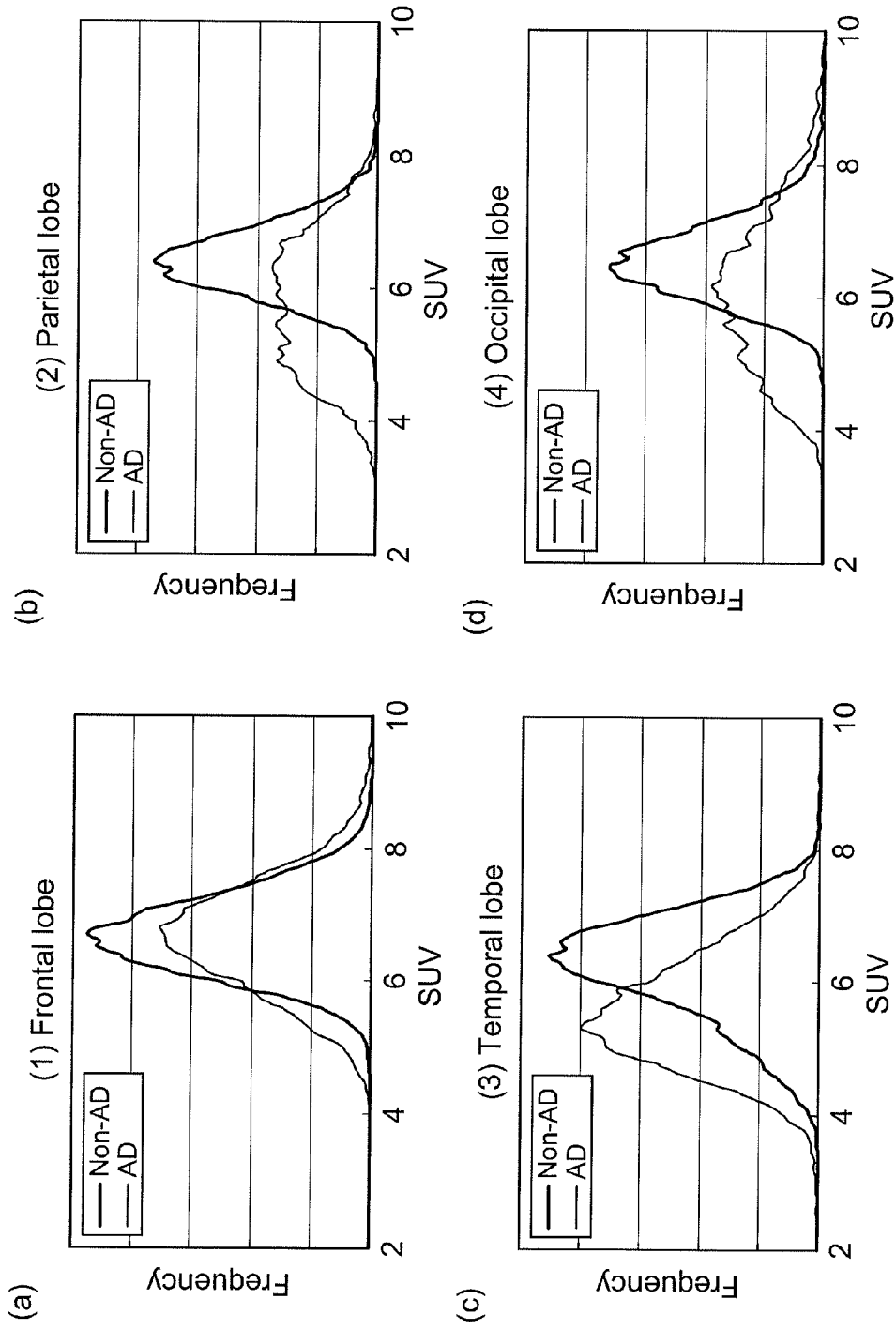
FIG. 10 is a histogram of SUV of an Alzheimer's diseased brain and a normal brain, for each brain region.
Figure 11:
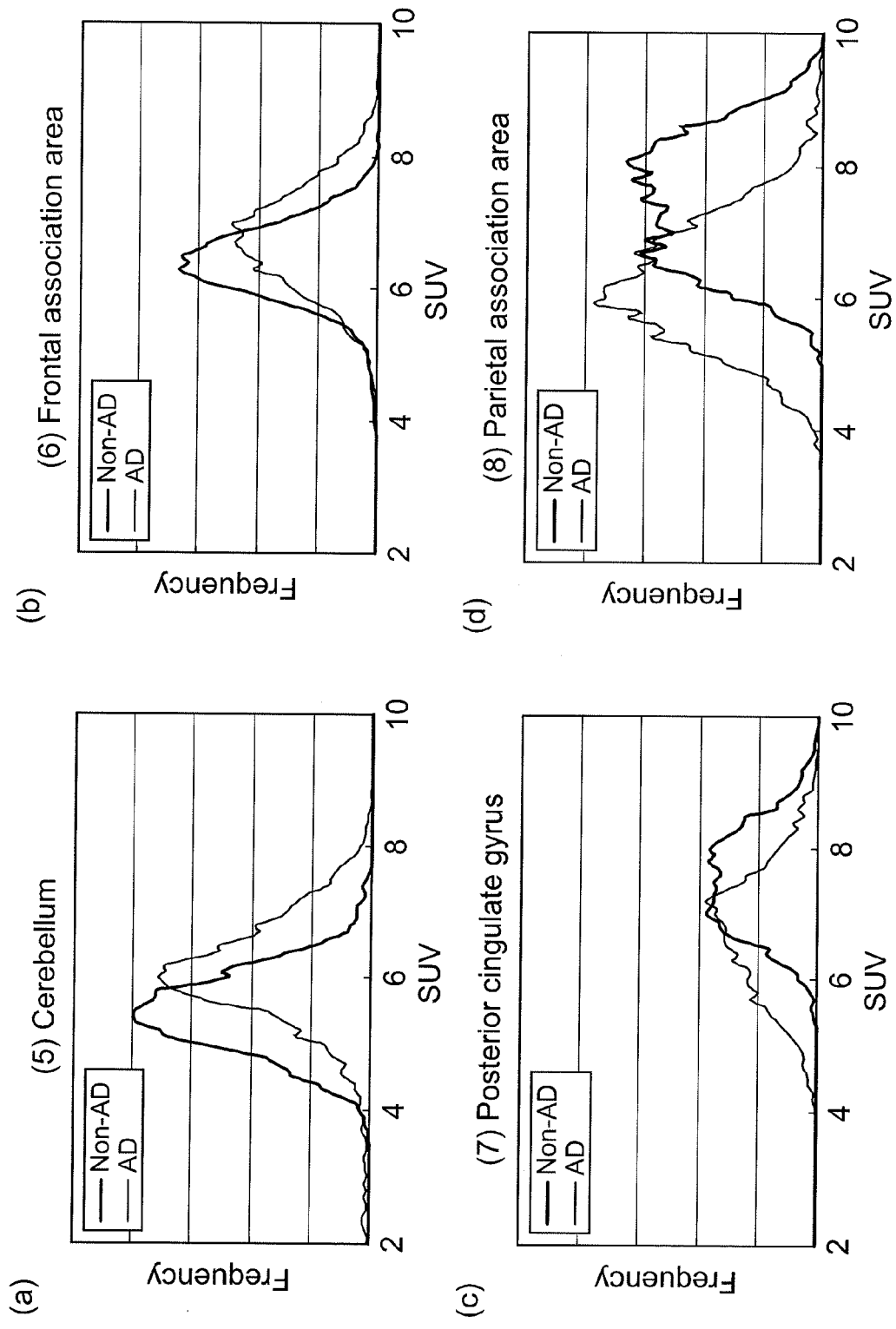
FIG. 11 is a histogram of SUV of an Alzheimer's diseased brain and a normal brain, for each brain region.

Further, FIG. 10 and FIG. 11 are histograms (of an average of a plurality of examined persons) of SUV of an Alzheimer's diseased brain (indicated by AD in the figure) and a normal brain (indicated by Non-AD in the figure), for each region of the brain shown in FIG. 8. As can also be seen from the above-described FIGS. 9 to 11, the difference in SUV detected between an Alzheimer's diseased brain and a normal brain differs depending on the site. Specifically, as described in the explanation in FIG. 6 using the Z score, there is a great difference in parietal lobe, temporal lobe, posterior cingulate gyms, and parietal association area between an Alzheimer's diseased brain and a normal brain.

At this time, diagnosis of the brain disease in which the image of the whole brain is uniquely processed is considered. FIG. 12(*a*) is a graph showing an average value (vertical axis) of SUV of an Alzheimer's diseased brain and a normal brain, for each of a plurality of examined persons, calculated from the above-described acquired image when the whole brain is a target. FIG. 12(*a*) is a graph with data obtained from 23 examples of a normal brain and 24 examples of an Alzheimer's diseased brain. Values in this graph are whole pixel conversion values evaluated from an average value $N_{ave}$ of the sample data of the average value of the pixel value of a plurality of normal brains and a standard deviation $NL_{SD}$ thereof, as described above. That is, these values are obtained by evaluating a whole pixel conversion value $NL_n'$ of an average value $NL_n$ of the pixel value of the acquired image (sample data) of a normal brain and a whole pixel conversion value $AD_m'$ of an average value $AD_m$ of the pixel value of the acquired image (sample data) of an Alzheimer's diseased brain, respectively, according to the following equation.

$$NL_n' = \frac{1}{NL_{SD}} \times NL_n - \frac{NL_{ave}}{NL_{SD}}, \qquad \text{[Equation 2]}$$

$$AD_m' = \frac{1}{NL_{SD}} \times AD_m - \frac{NL_{ave}}{NL_{SD}}$$

In the example of the graph shown in FIG. 12(*a*), it is possible to diagnose whether the brain suffers from Alzheimer's disease by setting a threshold value, for example. When a value is larger than the threshold value, the brain is determined to be a normal brain, and when the value is equal to or less than the threshold value, the brain is determined to suffer from Alzheimer's disease. In this case, however, even when the examined person suffers from brain disease, the brain may be determined to be a normal brain (no brain disease) because the value is larger than the threshold value. A ratio by which it is possible to correctly diagnose that the examined person suffers from brain disease in the case of presence of brain disease is called sensitivity. Further, even in the case of a normal brain (no brain disease), there is a case where the presence of brain disease is determined when the value falls below the threshold value. A ratio by which it is possible to correctly diagnose that the examined person is not suffering from brain disease in the case of a normal brain is called specificity. When the threshold value is decreased, the specificity is improved (on the other hand, the sensitivity is decreased), and when the threshold value is increased, the sensitivity is improved (on the other hand, the specificity is decreased).

A graph (called Receiver Operating Characteristic (ROC) curve) indicating a relationship between the sensitivity and the specificity, and the above-described threshold value when the data in FIG. 12(*a*) is used is shown in FIG. 12(*b*). In the graph of FIG. 12(*b*), a horizontal axis indicates 1-specificity, and a vertical axis indicates the sensitivity. The graph is obtained by plotting values of the sensitivity corresponding to the threshold value and the 1-specificity. Generally, as the diagnostic outcome, it is preferable that the sensitivity be as close as possible to 1 and the 1-specificity be as close as possible to 0, and thus, a graph in which the plotted line is located in the upper left as much as possible can demonstrate an excellent diagnosis capability. For example, when the threshold value is placed at individual pixel conversion value=−1, the sensitivity is 0.83 and the specificity is 0.78 (indicated by a circle in the graph), as shown in FIG. 12(b).

Figure 13:
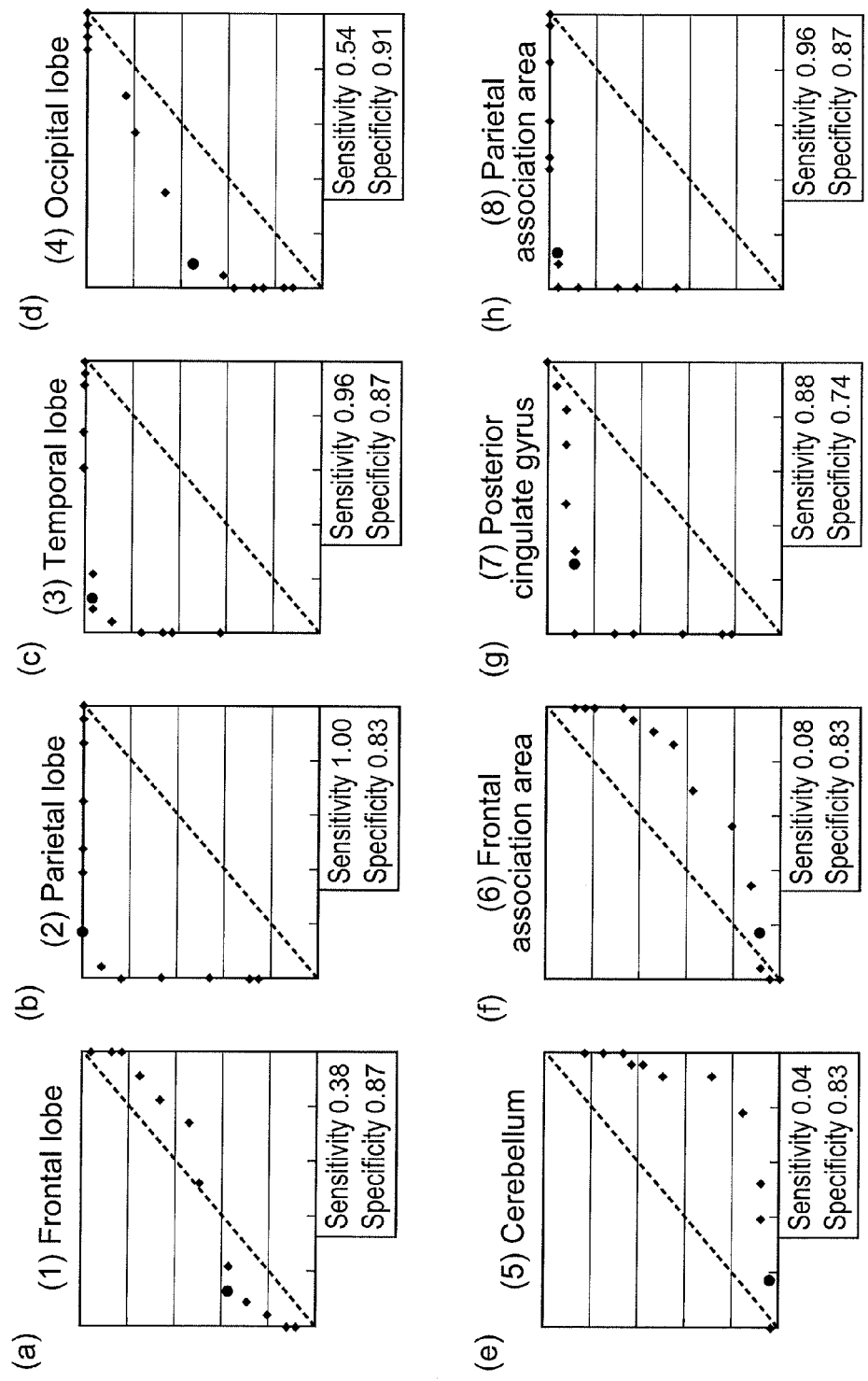
FIG. 13 is a graph showing a relationship between a threshold value, and a sensitivity and a specificity, for each brain region.

The above-described sensitivity and the specificity of each region of the brain can also be derived. Graphs indicating a relationship between the threshold value, and the sensitivity and the specificity, for each region of the brain shown in FIG. 8, and the sensitivity and the specificity when the threshold value is placed at the individual pixel conversion value=−1 are shown in FIG. 13. The sensitivity of each region at this time is as follows:

TABLE 1

| ROI (region) | Sensitivity |
| --- | --- |
| Whole brain | 0.83 |
| (1) Frontal lobe | 0.38 |
| (2) Parietal lobe | 1.00 |
| (3) Temporal lobe | 0.96 |
| (4) Occipital lobe | 0.54 |
| (5) Cerebellum | 0.04 |
| (6) Frontal association area | 0.08 |
| (7) Posterior cingulate gyrus | 0.88 |
| (8) Parietal association area | 0.96 |

The above-described sensitivity can be used as the weight coefficient kn used when the whole index value is derived. FIG. 14(a) shows a graph in which the sensitivity is used as the weight coefficient and the whole index value is derived from the sample data of a normal brain and an Alzheimer's diseased brain. Further, a graph showing a relationship between the threshold value, and the sensitivity and the specificity, when the diagnosis is performed using the whole index value, is shown in FIG. 14(b). Similar to the above case, when the threshold value is placed at the whole pixel conversion value=−1, the sensitivity is 1.00 and the specificity is 0.87 (indicated by a circle in the graph), as shown in FIG. 14(b). As described above, it can be seen that the sensitivity of the diagnosis is improved when the diagnosis is performed when a plurality of regions are set and the whole index value on which SUV of each region is weighted is used rather than being determined using SUV of the whole brain.

Upon diagnosis using the above-described weight coefficient, the diagnosis unit 15 may employ, as the threshold value, the individual pixel conversion value=−1 used when the weight coefficient is derived, or may also employ the threshold value corresponding to the point located at the upper leftmost along the ROC curve of the whole index value.

Further, in the above-described case, the sensitivity when the threshold value is placed at the individual pixel conversion value=−1 is utilized as the weight coefficient; however, the sensitivity at a previously set arbitrary value (for example, the individual pixel conversion value=−2), or the sensitivity corresponding to the point located at the upper leftmost along the ROC curve may be utilized, for example. Similarly, the specificity can be utilized as the weight coefficient. Moreover, based on the knowledge of the doctor, etc., the weight coefficient itself may be set previously and arbitrarily.

Moreover, the above may be combined, as described below, to derive the weight coefficient, and the resultant weight coefficient may be used.

$$\text{Weight coefficient } kn = kn_{sen} + kn_{spc} + kn_{Dr}$$

In the equation, $kn_{sen}$ denotes the sensitivity calculated using a predetermined threshold value, etc., as described above. $kn_{spc}$ denotes the specificity calculated using a predetermined threshold value, etc., as described above. $kn_{Dr}$ denotes the weight coefficient set by the doctor, etc. Further, any two of the above three values may also be used.

Moreover, as the threshold value used for the diagnosis by the diagnosis unit 15, the previously set threshold value (for example, in the above case, the whole pixel conversion value=−1) may be used, or the threshold value corresponding to the point located at the upper leftmost along the ROC curve, as shown in FIG. 14, obtained by the whole index value when the sample data is used may also be used.

The weight coefficient and the threshold value are set before the diagnosis on the examined person by using a plurality of sample data items with the brain disease and a plurality of sample data items without the brain disease, as described above. The larger the number of sample data, the more preferable. Specifically, desirably, about several tens of examples of the sample data of a normal brain and the brain with a cerebral disease are prepared. Moreover, the sample data of the same in generation and gender as the examined person are desirably used. Further, the sample data is desirably formed of an image acquired at the same facility or in the same type of machine. Types of brain disease may be prepared in plural, for example, several tens of examples of the sample data of a brain disease A and several tens of examples of the sample data of a brain disease B. Thus, the configuration of the brain disease diagnosis system 1 according to the embodiment has been explained.

Subsequently, by using a flowchart in FIG. 15, processing executed by the brain disease diagnosis system 1 will be explained. This processing is executed when a brain disease of the examined person is diagnosed by the brain disease diagnosis system 1.

In the brain disease diagnosis system 1, first, the examined person's slice image (FDG-PET image) is imaged and acquired by the PET machine 123. Further, together with the acquisition of the slice image, the information indicating the age of the examined person is input in a corresponding manner (S01). The examined person's slice image taken is input from the PET machine 123 to the diagnosis server 10 via the gateway server 60 (S02).

In the diagnosis server 10, the slice image is received by the acquiring unit 11. In this case, when the foregoing slice image is an entire body image, the diagnosis server 10 automatically cuts out only a head region necessary for the diagnosis (S03). When the foregoing slice image is the head region only, the automatic extraction of the head region (S03) is not necessary. Subsequently, the anatomic standardization by the 3DSSP processing is performed on the slice image by the acquiring unit 11 so that the standard brain image is produced (S04). Moreover, the mask processing may be performed on the standard brain image by the acquiring unit 11 so as to extract the image data inside a brain.

On the other hand, the imaging processing is further executed by the acquiring unit 11. First, the correction processing is performed on the standard brain image (S05). The correction processing is performed so that the average of the pixel values of a whole brain is a previously set predetermined value, as described above. Subsequently, the 3DSSP processing is performed on the corrected standard brain image by the acquiring unit 11 so as to produce the brain surface projection image (S06). The above-described standard brain image and the brain surface projection image are converted to the acquired image which is input from the acquiring unit 11 to the region setting unit 12.

Subsequently, a plurality of regions are set on the standard brain image and the brain surface projection image by the region setting unit 12 (S07). The regions are set based on the previous setting, etc., as described above. Each image data and the set region information are input from the region setting unit 12 to the individual index value calculating unit 13.

Subsequently, the histogram data for each set region, as shown in FIG. 10, FIG. 11, etc., is extracted from the image data of the above-described acquired image by the individual index value calculating unit 13 (S08). The histogram data is data about the frequency of the pixel for each SUV. Subsequently, the individual index value for each region is calculated from the histogram data by the individual index value calculating unit 13 (S09). The calculated individual index value is input to the whole index value calculating unit 14 from the individual index value calculating unit 13.

Subsequently, the respective individual index values of the regions are weighted by the whole index value calculating unit 14, and thereby, the whole index value is calculated (S10). The weight coefficient used for calculation of the whole index value is previously calculated from the index value of the sample data having the brain disease and the sample data not having the brain disease, as described above, and stored in the whole index value calculating unit 14. However, there is no need that the weight coefficient is previously calculated and the coefficient may be calculated at this timing of S10. Two whole index values are calculated from the standard brain image and the brain surface projection image. The calculated whole index values are input to the diagnosis unit 15 from the whole index value calculating unit 14.

Subsequently, a brain disease of the examined person is diagnosed based on the whole index value by the diagnosis unit 15 (S11). Specifically, as described above, by comparing the threshold value previously stored in the diagnosis unit 15 and the whole index value, whether the examined person suffers from a brain disease that is subject to examination is diagnosed. In this case, two diagnoses, i.e., diagnosis based on the standard brain image and that based on the brain surface projection image, are performed. The information indicating the diagnosis outcome is input from the diagnosis unit 15 to the output unit 16. In this case, if there are a plurality of housed brain disease teacher data items for each type of brain disease, then the steps in S07 to S11 are repeatedly executed.

Subsequently, the information indicating the diagnosis outcome by the diagnosis unit 15 is output from the output unit 16 to the storages 20 and accommodated in the storages 20 (S12). The above-described information accommodated in the storages 20 is acquired by the client 100, the viewer 110, etc., of the brain disease diagnosis system 1, and displayed. Further, each image or information generated by the above-described processing is also accommodated in the storages 20, and utilized similar to the information indicating the diagnosis outcome.

On the other hand, by the acquiring unit 11, the imaging processing as described below is further executed on the standard brain image generated in S04. First, from the standard brain image, the brain surface projection image 204 is generated by the 3DSSP processing (S21). Then, the brain surface projection image of a normal brain for which the generation is the same as that of the examined person accommodated in the storages 20 is acquired (S22). Subsequently, the brain surface projection image of a normal brain is used to calculate the Z score for each pixel of the brain surface projection image of the examined person. It is noted that the average value and the standard deviation of the pixel values, used upon calculation of the Z score may be calculated at this timing, or those which are previously calculated and stored in the storages 20, etc., may be utilized. Subsequently, the brain image (difference image) in which the pixel value is the calculated Z score (the value corresponding thereto) is generated (S23).

Each of the above-described images generated by the acquiring unit 11 is output to the storages 20 via the output unit 16 and accommodated in the storages 20 (S24). Specifically, the slice image (head PET raw image) imaged by the PET machine 123, the anatomically-standardized standard brain image, the brain surface projection image, and the difference image using the Z score are accommodated in the storages 20. The above-described information accommodated in the storages 20 is acquired by the client 100, etc., of the brain disease diagnosis system 1 and displayed.

The information and the image accommodated in the storages 20 in steps S12 and S24 are displayed on the client 100, the viewer 110, etc., as described above. The doctor, etc., refer to (interpret the radiogram of) the information and the image in order to make the most use of these in diagnosis, medical treatment, etc (S31). Thus, the processing executed by the brain disease diagnosis system 1 has been explained.

As described above, in the brain disease diagnosis system 1 according to the embodiment, based on the image of the brain of the examined person, a brain disease of the examined person is diagnosed. In this system 1, a plurality of regions are set to the brain image, and the individual index values based on the pixel value are calculated for each of the plurality of regions. Then, each of the individual index values is weighted so that the whole index value is calculated after which the above-described diagnosis is performed from the whole index value. Therefore, according to the brain disease diagnosis system 1 according to the embodiment, it is possible to make a determination while considering the influence of a brain disease for each brain region, and also possible to diagnose with a manner similar to the doctor's interpretation of a radiogram (doctor's eyes). As a result, it is possible to perform a more accurate and detailed diagnosis of a brain disease. Further, diagnostic mistakes can be decreased. As a result of the utilization of the automatic diagnosis outcome, a burden imposed when the doctor interprets the radiogram is alleviated and this outcome can be referred to as additional information when the doctor interprets the radiogram.

Moreover, for example, in the method described in Patent Literature 1, the ROI is set only to the site where there is a significant difference between the prepared two groups and the other site is not subject to the determination. Thus, a case of a brain disease that does not match the ROI pattern of the teacher data cannot be easily detected. On the other hand, in this embodiment, in the case of a brain disease, a site that is specifically decreased and other sites can be considered as the target for determination. Besides, the ROI is set to a site where the doctor seldom observes, and thereby, the data of such a site comes to be considered. As a result, it is possible to perform a more accurate and detailed diagnosis of a brain disease. That is, as compared to the conventional technology, it becomes possible to perform a more comprehensive, highly accurate diagnosis.

Further, as in the embodiment, when the sample data having the brain disease and that not having the brain disease are utilized and the threshold value or the weight coefficient used at the time of the diagnosis is obtained, the determination criteria or the weighting can be made more suitable and the diagnosis of a brain disease can be performed more accurately and in more detail. For example, a large weighting can be applied to a range where a brain disease to be diagnosed is greatly influenced. Moreover, a successive numerical value such as the sensitivity and the specificity by using the sample data is employed, and thus, a successive (score and index value) evaluation, i.e., the level of similarity to the ROI pattern of the teacher data, can be enabled. However, the threshold value or the weight coefficient may be set by the doctor, etc., and the sample data may not always be used.

If the brain image is corrected, as described above, then a brain disease can be suitably diagnosed by removing individual variability, etc., of the brain of the examined person. Further, if the brain image is anatomically standardized, then a brain disease can be suitably diagnosed by facilitating the processing of the brain image.

Moreover, the threshold value or the weighting is desirably applied depending on the age of the examined person. Although, generally, a state of a brain changes according to age, as described above, according to this configuration, it is possible to appropriately diagnose a brain disease according to age.

As in the embodiment, the diagnosis using the brain surface projection image is desirable. According to this configuration, based on the brain surface image that facilitates the diagnosis for some type of brain disease, the diagnosis can be performed. Moreover, in this embodiment, the diagnosis is performed based on the two images, i.e., the standard brain image and the brain surface projection image; however, the diagnosis may be performed by using either one of the images.

Further, by providing that the modalities 121 to 123 are included in the brain disease diagnosis system 1, as in the embodiments, the brain image can be reliably acquired, and thus, the present invention can be reliably implemented. However, in the brain disease diagnosis system 1, as long as the brain image is acquired, the diagnosis can be performed. Because of this, a device for imaging is not always necessary.

In this embodiment, the case where the PET machine 123 is primarily used as the modalities has been explained; however, besides, the CT machine 121, the MRI machine 122, a SPECT machine (not shown), etc., may be used. In this case, as the brain image, the PET machine 123 can detect a metabolism and a blood flow; the CT machine 121 a brain atrophy, a brain neoplasm, a brain infarction, and a brain bleeding; the MRI machine 122 a brain atrophy, a brain neoplasm, a brain infarction, and a brain bleeding; the SPECT machine a brain blood perfusion scintigraphy, respectively. Therefore, the modalities according to a brain disease to be diagnosed are preferably selected.

Further, in this embodiment, the example in which Alzheimer's disease is diagnosed has been explained; however, other brain diseases may be diagnosed. For example, a cerebral vascular disturbance, a dementia, and a brain death, or other degenerative neurological disorders or psychological disorders or encephalitis may be diagnosed. Moreover, regarding the brain atrophy, the brain neoplasm, the brain infarction, and the brain bleeding, it is possible to diagnose which portion experiences an abnormality.

Further, the brain diseases as described below can be diagnosed (the parenthetic sites below are brain sites closely related to the brain diseases, and can be referred to for the weighting, etc.). More specifically, the examples include: frontotemporal dementia (frontal lobe, temporal lobe); corticobasal degeneration (frontal lobe, parietal lobe); progressive supranuclear palsy (frontal lobe, interior of higher frontal lobe); amyotrophic lateral sclerosis (frontal lobe, primary sensorimotor area); epilepsy (temporal lobe, others); Alzheimer-type dementia (temporal lobe, parietal lobe, posterior cingulate gyms, hippocampus); mild cognitive impairment (MCI) (temporal lobe, parietal lobe, posterior cingulate gyms, hippocampus); dementia with Lewy bodies (parietal lobe, posterior cingulate gyms, occipital lobe); mitochondrial encephalomyopathy (MELAS) (occipital lobe); multiple sclerosis (occipital lobe); Parkinson's disease (occipital lobe); Huntington's disease (basal ganglia); Wilson's disease (basal ganglia); Binswanger's disease (white matter); hydrocephalus (white matter); cerebrovascular disease (diffuse (epidemic) decreased cerebellar blood flow); degenerative metabolic defect (spinocerebellar degeneration) (diffuse decreased cerebellar blood flow); multiple system atrophy (olivopontocerebellar degeneration) (diffuse decreased cerebellar blood flow); dentatorubropallidoluysian atrophy (DRPLA) (diffuse decreased cerebellar blood flow); cerebrotendinous xanthomatosis (diffuse decreased cerebellar blood flow); medicinal poisoning (diffuse decreased cerebellar blood flow); cerebellar encephalitis (diffuse decreased cerebellar blood flow); radiation exposure (diffuse decreased cerebellar blood flow); infectious disease (neurosyphilis, Creutzfeldt-Jakob disease, Wernicke's encephalopathy) (abnormal spread in a wide cerebral range); subacute sclerosing panencephalitis (SSPE) (abnormal spread in a wide cerebral range); acute disseminated encephalomyelitis (ADEM) (abnormal spread in a wide cerebral range); medicinal poisoning (abnormal spread in a wide cerebral range, a serotonergic system lowers a corpus striatum); hypoxemia (abnormal spread in a wide cerebral range); carbon monoxide poisoning (abnormal spread in a wide cerebral range); Binswanger's disease (abnormal spread in a wide cerebral range); Gerstmann's syndrome (parietal lobe); amyotrophic lateral sclerosis (primary sensorimotor area); inferior homonymous quadrantanopia (parietal lobe); hemispatial neglect (parietal lobe in minor hemisphere); ataxia (cerebellum); gait ataxia, truncal ataxia (upper cerebellar vermis); subcortical arteriosclerotic encephalopathy (site with blood vessel infarction); other cognition disorders (endocrine, infection, tumor, external injury, and hydrocephalus) (corresponding site); other functional disorders (hearing, sight, aphasia, semantic aphasia, etc.) (corresponding site); Parkinson's disease (dopamine medicine (raclopride, β-CFT) lowers a corpus striatum); stimulant addict (serotonin medicine (McN5652, DASB) lowers a corpus striatum); Alzheimer-type dementia (PIB increases integration); and mild cognitive impairment (MCI) (PIB increases integration).

REFERENCE SIGNS LIST

1 . . . brain disease diagnosis system, 10 . . . diagnosis server, 11 . . . acquiring unit, 12 . . . region setting unit, 13 . . . individual index value calculating unit, 14 . . . whole index value calculating unit, 15 . . . diagnosis unit, 16 . . . output unit, 20 . . . storage, 30 . . . load balancer, 40 . . . image server, 50 . . . business server, 60 . . . gateway server, 70 . . . switching hub, 80 . . . load balancer, 100 . . . client, 110 . . . viewer, 121 to 123 . . . modalities (121 . . . CT machine, 122 . . . MRI machine, 123 . . . PET machine), 130 . . . switching hub.

The invention claimed is:

1. A brain disease diagnosis system for diagnosing a brain disease of an examined person, comprising:

acquiring means for acquiring a brain image of the examined person so as to obtain an acquired image;

region setting means for setting a plurality of regions in the acquired image acquired by the acquiring means;

individual index value calculating means for calculating an individual index value based on a pixel value of the acquired image, in each of the plurality of regions set by the region setting means;

whole index value calculating means for calculating a whole index value by weighting the individual index value of each of the plurality of regions calculated by the individual index value calculating means;

diagnosis means for diagnosing the brain disease of the examined person based on the whole index value calculated by the whole index value calculating means; and output means for outputting information indicating a diagnosis outcome issued by the diagnosis means.

2. The brain disease diagnosis system according to claim 1, wherein the diagnosis means diagnoses the brain disease of the examined person by comparing a threshold value obtained based on an index value of sample data having the brain disease and an index value of sample data not having the brain disease and the whole index value calculated by the whole index value calculating means.

3. The brain disease diagnosis system according to claim 1, wherein the whole index value calculating means performs the weighting based on the index value of the sample data having the brain disease and the index value of the sample data not having the brain disease.

4. The brain disease diagnosis system according to claim 1, wherein the acquiring means corrects the image based on the pixel value of the acquired brain image so as to obtain the acquired image.

5. The brain disease diagnosis system according to claim 1, wherein the acquiring means also acquires information indicating the age of the examined person, and the diagnosis means diagnoses the brain disease of the examined person according to the age of the examined person indicated by the information acquired by the acquiring means.

6. The brain disease diagnosis system according to claim 1, wherein the acquiring means anatomically standardizes the acquired brain image so as to obtain the acquired image.

7. The brain disease diagnosis system according to claim 1, further comprising imaging means for imaging the brain image of the examined person, wherein the acquiring means acquires the image imaged by the imaging means.

8. The brain disease diagnosis system according to claim 7, wherein the imaging means images a slice image of a brain of the examined person as the brain image of the examined person, and the acquiring means produces from the slice image imaged by the imaging means a brain surface projection image obtained by projecting a brain surface of the brain so as to obtain the acquired image.

* * * * *

UNITED STATES PATENT AND TRADEMARK OFFICE
CERTIFICATE OF CORRECTION

PATENT NO.       : 8,676,294 B2
APPLICATION NO. : 13/002371
DATED            : March 18, 2014
INVENTOR(S)      : Kakimoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 293 days.

Signed and Sealed this
Twenty-ninth Day of September, 2015

Michelle K. Lee
*Director of the United States Patent and Trademark Office*